United States Patent
Lennartz et al.

(10) Patent No.: US 12,156,691 B2
(45) Date of Patent: Dec. 3, 2024

(54) SURGICAL SYSTEM AND METHODS FOR TREATING TISSUE

(71) Applicant: Covidien LP, Mansfield, MA (US)

(72) Inventors: Amanda H. Lennartz, Erie, CO (US); Daniel A. Joseph, Golden, CO (US); Jennifer R. McHenry, Denver, CO (US); Cornelia F. Twomey, Longmont, CO (US); David M. Garrison, Longmont, CO (US); Tyler J. Bagrosky, Arvada, CO (US); Robert H. Wham, Boulder, CO (US); Jing Zhao, Superior, CO (US); Erin E. Wehrly, Longmont, CO (US)

(73) Assignee: Covidien LP, Mansfield, MA (US)

( * ) Notice: Subject to any disclaimer, the term of this patent is extended or adjusted under 35 U.S.C. 154(b) by 392 days.

(21) Appl. No.: 17/211,465

(22) Filed: Mar. 24, 2021

(65) Prior Publication Data

US 2021/0330375 A1    Oct. 28, 2021

Related U.S. Application Data

(60) Provisional application No. 63/013,815, filed on Apr. 22, 2020.

(51) Int. Cl.
*A61B 18/14* (2006.01)
*A61B 90/00* (2016.01)
*A61B 18/00* (2006.01)

(52) U.S. Cl.
CPC .......... *A61B 18/1445* (2013.01); *A61B 90/06* (2016.02); *A61B 2018/0063* (2013.01); *A61B 2018/00642* (2013.01); *A61B 2018/00666* (2013.01); *A61B 2090/065* (2016.02)

(58) Field of Classification Search
CPC .................................................. A61B 18/1445
See application file for complete search history.

(56) References Cited

U.S. PATENT DOCUMENTS

| | | |
|---|---|---|
| 7,731,717 B2 | 6/2010 | Odom et al. |
| 7,776,037 B2 | 8/2010 | Odom |
| 8,382,754 B2 | 2/2013 | Odom et al. |
| (Continued) | | |

OTHER PUBLICATIONS

"Calculate Angular Diameter", May 10, 2010, <https://rechneronline.de/sehwinkel/angular-diameter.php> (Year: 2010).*

*Primary Examiner* — Linda C Dvorak
*Assistant Examiner* — Ryan T Clark

(57) ABSTRACT

An electrosurgical instrument includes an end effector assembly including first and second jaw members. At least one of the first or second jaw members is movable about a pivot relative to the other from a spaced-apart position to an approximated position to grasp tissue between first and second opposed surfaces of the first and second jaw members, respectively. The electrosurgical instrument further includes an interface configured to provide a feedback related to a size of tissue grasped by the first and second jaw members. At least one of the first or second jaw members includes a touch sensor configured to sense a touch span where the tissue touches the at least one of the first or second opposed surfaces. The end effector assembly further includes an angle sensor configured to sense an angle α about the pivot between the first and second opposed surfaces.

22 Claims, 7 Drawing Sheets

(56) References Cited

U.S. PATENT DOCUMENTS

| | | |
|---|---|---|
| 8,439,913 B2 | 5/2013 | Horner et al. |
| 9,247,988 B2 | 2/2016 | McKenna et al. |
| 9,603,652 B2 | 3/2017 | Carlton et al. |
| 9,642,665 B2 | 5/2017 | Weinberg et al. |
| 9,839,467 B2 | 12/2017 | Harper et al. |
| 9,918,783 B2 | 3/2018 | Horner et al. |
| 10,117,705 B2 | 11/2018 | Chernov et al. |
| 10,130,413 B2 | 11/2018 | Brandt et al. |
| 10,245,104 B2 | 4/2019 | McKenna et al. |
| 10,335,226 B2 | 7/2019 | Harper et al. |
| 2002/0062123 A1* | 5/2002 | McClurken ........ A61B 18/1442 606/34 |
| 2009/0204114 A1 | 8/2009 | Odom |
| 2010/0217264 A1 | 8/2010 | Odom et al. |
| 2012/0136354 A1* | 5/2012 | Rupp ................ A61B 18/1206 606/51 |
| 2012/0143182 A1* | 6/2012 | Ullrich ............... A61B 18/1445 606/49 |
| 2015/0223868 A1 | 8/2015 | Brandt et al. |
| 2016/0045248 A1 | 2/2016 | Unger et al. |
| 2016/0089198 A1 | 3/2016 | Arya et al. |
| 2016/0346034 A1 | 12/2016 | Arya et al. |
| 2017/0000553 A1* | 1/2017 | Wiener .............. A61B 18/1445 |
| 2017/0079740 A1 | 3/2017 | Hufnagel et al. |
| 2017/0215943 A1 | 8/2017 | Allen, IV |
| 2017/0215944 A1 | 8/2017 | Keffeler |
| 2019/0083168 A1 | 3/2019 | Wham |
| 2019/0282296 A1 | 9/2019 | Harper et al. |

\* cited by examiner

SURGICAL SYSTEM AND METHODS FOR TREATING TISSUE

CROSS-REFERENCE TO RELATED APPLICATIONS

This application claims the benefit of and priority to U.S. Provisional Patent Application No. 63/013,815, filed on Apr. 22, 2020, the entire contents of which are hereby incorporated herein by reference.

FIELD

The present disclosure is generally related to systems and methods for treating tissue.

BACKGROUND

Surgical operations might involve laparoscopic operations on tissue. During an operation, tissue can be cut, coagulated, and/or sealed. Various tissues require different mechanical and/or energy parameters based on the size, type, mass, etc. of the tissue. Thus, identification of the tissue facilitates treating the tissue.

SUMMARY

This disclosure generally relates to systems and methods for estimating a size (e.g., a radius, cross-sectional area, mass, etc.) of tissue prior to treatment of the tissue.

Provided in accordance with aspects of the disclosure is an electrosurgical instrument, which includes an end effector assembly including first and second jaw members. At least one of the first or second jaw members is movable about a pivot relative to the other from a spaced-apart position to an approximated position to grasp tissue between first and second opposed surfaces of the first and second jaw members, respectively. The electrosurgical instrument further includes an interface configured to provide a feedback related to a size of tissue grasped by the first and second jaw members. At least one of the first or second jaw members includes a touch sensor configured to sense a touch span where the tissue touches at least one of the first or second opposed surfaces. The end effector assembly further includes an angle sensor configured to sense an angle α about the pivot between the first and second opposed surfaces.

In an aspect of the disclosure, wherein the touch span is one position, and the touch sensor provides a distance D between the pivot and the one position of the at least one of the first or second opposed surfaces. The distance D and the angle α are used to estimate a diameter of the tissue as the size, S, by the following equation:

$$S=2*D*\tan(\alpha/2).$$

In another aspect of the disclosure, the touch sensor is a pressure sensor, a contact sensor, or a jaw latched closed sensor, which provides measurements when the first and second jaw members are locked closed. The locked closed state of the first and second jaw members may provide a consistent measurement from use to use.

In still another aspect, a cross-sectional area of the grasped tissue is calculated based on a length of the touch span and the angle α.

In still another aspect, a mass of the grasped tissue is calculated by multiplying the cross-sectional area, a width of the first or second jaw member and a density of the grasped tissue.

In still another aspect of the disclosure, the feedback indicates that the grasped tissue is ready to be sealed when the size of the grasped tissue is less than a first threshold. In aspects, the feedback is a green light.

In still another aspect of the disclosure, when the size of the grasped tissue is greater than or equal to the first threshold and less than a second threshold, the feedback indicates that the grasped tissue is ready to be sealed with different energy-delivery parameters than when the size is less than the first threshold. In aspects, the feedback is a yellow light.

In still another aspect of the disclosure, the feedback indicates that the grasped tissue cannot be sealed when the size is greater than or equal to the second threshold. In aspects, the feedback is a red light.

Provided in accordance with aspects of the disclosure is a method for controlling an electrosurgical instrument including an end effector assembly having first and second jaw members. At least one of the first or second jaw members is movable about a pivot relative to the other from a spaced-apart position to an approximated position to grasp tissue between first and second opposed surfaces of the first and second jaw members, respectively. The method includes moving the at least one of the first or second jaw members about the pivot to grasp tissue, sensing a touch span on at least one of the first or second opposed surfaces from the pivot, sensing an angle α between the first and second opposed surfaces about the pivot, estimating a size of the tissue based on the touch span and the angle, and providing a feedback based on the size of the tissue.

In an aspect of the disclosure, the touch span is one position, and the method further includes calculating a distance D between the pivot and the one position of the at least one of the first or second opposed surfaces. In aspects, a diameter of the tissue as the size, S, is estimated by the following equation: $S=2*D*\tan(\alpha/2)$.

In another aspect of the disclosure, the touch span is one position, and the method further includes calculating a distance D between the pivot and the one position of the at least one of the first or second opposed surfaces.

In still another aspect, estimating a size of the tissue includes calculating a cross-sectional area of the grasped tissue based on a length of the touch span and the angle α.

In still another aspect, estimating a size of the tissue includes calculating a mass of the grasped tissue as the size by multiplying the cross-sectional area, a width of at least one of the first or second jaw members and a density of the grasped tissue.

In another aspect of the disclosure, the feedback indicates that the grasped tissue is ready to be sealed when the size of the grasped tissue is less than a first threshold. In aspects, the feedback is a green light.

In another aspect of the disclosure, when the size is greater than or equal to the first threshold and less than a second threshold, the feedback indicates that the grasped tissue is ready to be sealed with different energy-delivery parameters than when the size is less than the first threshold. In aspects, the feedback is a yellow light.

In still yet another aspect of the disclosure, the feedback indicates that the grasped tissue cannot be sealed when the size is greater than or equal to the second threshold. In aspects, the feedback is a red light.

Provided in accordance with aspects of the disclosure is a nontransitory storage medium storing instructions that, when executed by a processor, cause the processor to perform a method for controlling an electrosurgical instrument including an end effector assembly having first and second jaw members. At least one of the first or second jaw members is movable about a pivot relative to the other from a spaced-apart position to an approximated position to grasp tissue between first and second opposed surfaces of the first and second jaw members, respectively. The method includes moving at least one of the first or second jaw members about the pivot to grasp tissue, sensing a touch span on at least one of the first or second opposed surfaces, sensing an angle α between the first and second opposed surfaces about the pivot, estimating a size of the tissue based on the touch span and the angle, and providing a feedback based on the size of the tissue.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Surgical operations often involve treatment of tissue that includes vessels. When the tissue is to be cut or treated, the vessels in the tissue often need to be sealed so as to prevent blood or body fluid from leaking. Based on the size of the tissue, different mechanical (e.g., pressure, gap distance, etc.) and/or energy delivery parameters (e.g., an amount of energy, a period of energy delivery, etc.) are required. When the tissue is small and high energy is applied, for example, there is a risk that the tissue may not be sealed but desiccated. On the other hand, when the tissue is large and low energy is applied, for example, the tissue might not be fully sealed. Thus, estimation of the size of the tissue prior to delivery of energy and taking into account the same during the surgical operation would facilitate performing the surgical operations. The present disclosure provides systems and methods for estimating a size of tissue prior to surgical operations.

Figure 1:
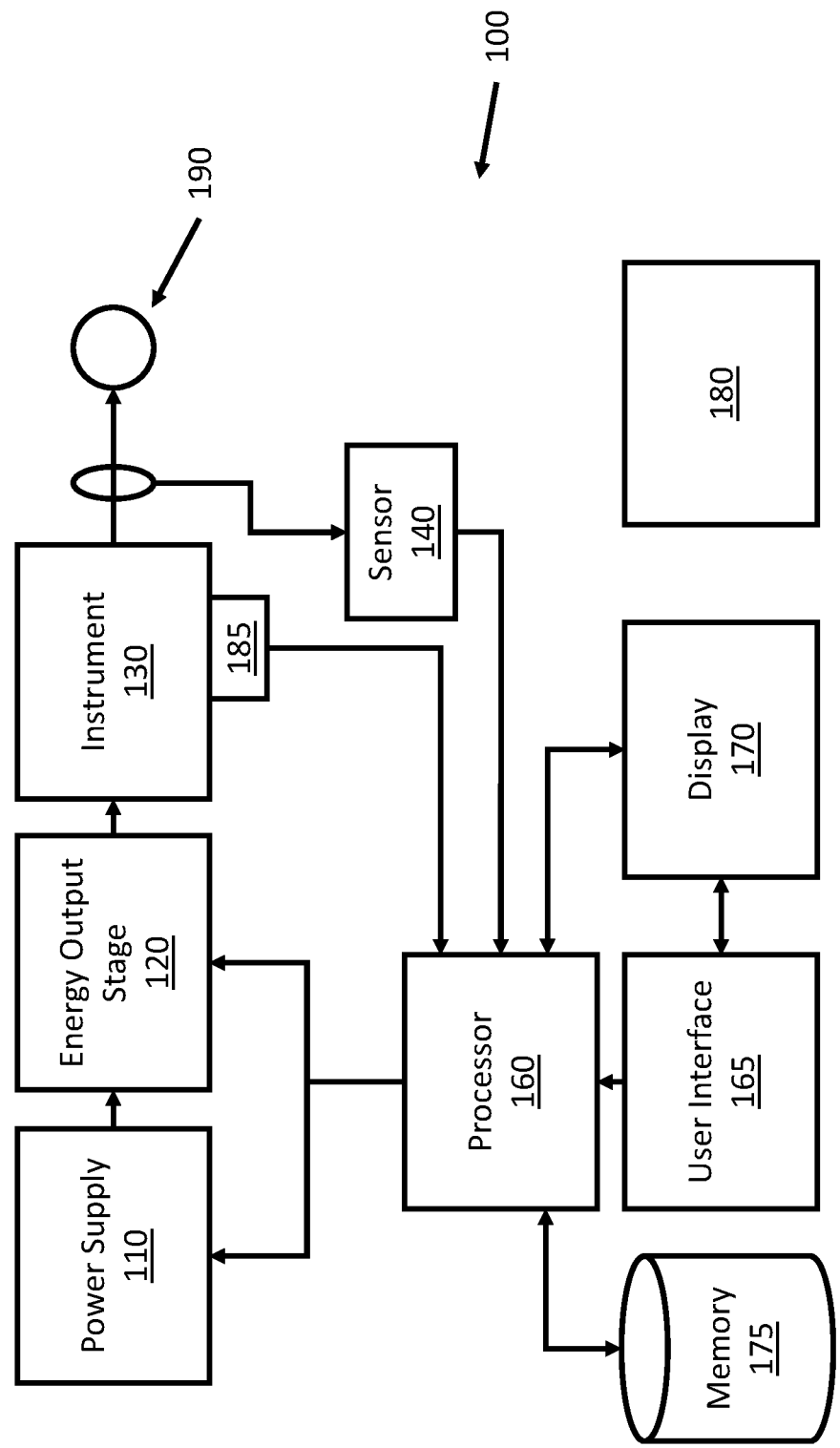
FIG. 1 is a block diagram of a surgical system for treating tissue according to aspects of the present disclosure.

FIG. 1 shows a block diagram of a surgical system 100 for treating tissue and estimating a size thereof according to aspects of the present disclosure. The surgical system 100 may use any type of energy to treat tissue including mechanical energy, acoustic energy, thermal energy, ultrasonic energy, electrical energy, or electromagnetic (EM) energy (e.g., optical energy or radio frequency (RF) energy). The surgical system 100 may use EM waves to identify a location of one or more elements of the surgical system 100 and synchronize the patient with a three-dimensional (3D) model of a patient. Further, the surgical system 100 may identify a location of tissue of interest, synchronize the identified location of the tissue with the 3D model, and display a graphical representation of the tissue at the corresponding location in the 3D model in an augmented way. By doing the above, the surgical system 100 helps clinicians to estimate a size of the tissue and perform surgical operations without unintentionally cutting or otherwise damaging vessels, e.g., blood vessels or bile ducts, or other tissue structures.

Prior to or concurrently with surgical operations, a three-dimensional (3D) model is generated to visually display patient's anatomy. During an imaging/planning stage, a computer utilizes computed tomography (CT) image data or other image data in the Digital Imaging and Communications in Medicine (DICOM) format, for generating and viewing a 3D model of the patient's body. In aspects, the 3D model may be generated in real time based on the live video. The 3D model and image data derived from the 3D model enables identification of the region of interest (automatically, semi-automatically or manually), and allows for the selection of a pathway to the region of interest. More specifically, the CT scans are processed and assembled into a 3D volume, which is then utilized to generate the 3D model of the patient's body. The surgical system 100 may include a memory 175 to store the 3D model or receive the 3D model from another computer, which has generated or stored the 3D model. The surgical system 100 may be coupled to a display 170 and cause the display 170 to display the 3D model on its screen.

The surgical system 100 may include a power supply 110, an energy output stage 120, and an instrument 130. The power supply 110 supplies power to the energy output stage 120, which generates energy and provides the energy to the instrument 130. The instrument 130, in turn, applies the generated energy to the tissue 190. For an RF-based tissue-sealing system, the energy output stage 120 generates RF energy and the instrument 130 applies the RF energy to the tissue 190 through at least one contact to seal the tissue 190. Various other types of instruments 130 may be encompassed in this disclosure as understood by a person having ordinary skill in the art.

Prior to delivery of the energy, the instrument 130 may include a surface sensor (e.g., a pressure sensor or a touch sensor) which is able to detect a touch span, i.e., the distance along a surface of the instrument 130 that is touched by tissue. Based on the detected touch span, a size of the tissue may be estimated. Further, based on the estimated size, a proper amount of energy may be calculated and supplied to treat the tissue. In an aspect, the size of the tissue may be a radius, diameter, cross-sectional area, and/or mass of the tissue. This is not meant to be exhaustive but can include other measures as readily appreciated by a person of ordinary skill in the art reading this disclosure.

The surgical system 100 may also include a sensor 140, a processor 160, a user interface 165, and display 170. The sensor 140 senses various parameters and/or properties of the RF energy applied by the instrument 130 at the operating site and transmits sensor signals representing the sensed parameters or properties of the RF energy to the processor

160. The processor 160 processes the sensor signals and generates control signals based on the processed sensor signals to control the power supply 110 and/or the energy output stage 120. For example, the processor 160 may regulate the voltage or current output from the power supply 110 or the energy output stage 120 based on the processed sensor signals.

The sensor 140 is configured to measure various electrical or electromechanical conditions at the operating site such as tissue impedance, changes in tissue impedance, tissue temperature, changes in tissue temperature, leakage current, applied voltage, and applied current. The sensor 140 continuously or intermittently measures one or more of these conditions so that the processor 160 can continually adjust the energy output from the power supply 110 and/or the energy output stage 120 during a sealing procedure. For example, in an RF-based vessel sealing, the sensor 140 may measure tissue impedance and the processor 160 may adjust the voltage generated by the energy output stage 120.

The user interface 165 is coupled to the processor 160 allowing a user to control various parameters of the energy applied to the tissue 190 during a surgical procedure. For example, the user interface 165 may allow a user to manually set, regulate and/or control one or more parameters of the energy delivered to the tissue 190, such as voltage, current, power, frequency, and/or pulse parameters, e.g., pulse width, duty cycle, crest factor, and/or repetition rate.

The processor 160 may be designed to execute software instructions, which are saved in the memory 175, for processing data received from the user interface 165 and for outputting control signals to the power supply 110 and/or the energy output stage 120. The software instructions may be uploaded to or stored in an internal memory of the processor 160, an internal or external memory bank accessible by the processor 160 and/or an external memory, e.g., an external hard drive, floppy diskette, or CD-ROM. Control signals generated by the processor 160 may be converted to analog signals by a digital-to-analog converter (DAC) (not shown) before being applied to the power supply 110 and/or energy output stage 120.

For RF-based tissue-sealing systems, the power supply 110 may be a high-voltage DC power supply that produces RF current. In these systems, the processor 160 transmits control signals to the power supply to control the magnitudes of the RF voltage and current output from the power supply 110. The energy output stage 120 receives the RF current and generates one or more pulses of RF energy. The processor 160 generates control signals to regulate the pulse parameters of the RF energy, such as pulse width, duty cycle, crest factor, and repetition rate. In other aspects, the power supply 110 is an AC power supply, and the energy output stage 120 may vary the waveform of the AC signal generated by the power supply 110 to achieve a desired waveform.

As described above, the surgical system 100 includes the user interface 165, which includes an input device, such as a keyboard or touch screen, through which a user enters data and commands. The data may include the type of instrument, the type of procedure, and/or the type of tissue. The commands may include target effective voltage, current, or power level, or other commands for controlling parameters of the energy that is delivered from the energy output stage 120 to the instrument 130.

In aspects, the user interface 165 may be incorporated into the display 170. For example, the display 170 may be touch sensitive and display graphical icons/representations to adjust various parameters. In such configurations, a clinician adjusts values of the various parameters by touching/holding/dragging icons on the display 170.

Continuing with reference to FIG. 1, when a patient is placed on a surgical table for receiving a surgical operation, an EM wave is generated by an EM wave generator 180. The generated EM wave surrounds the patient. An EM sensor 185, which is installed/fixed on the instrument 130 a predetermined distance from its distal tip or other point of reference, senses the strength of the EM wave at the position of the instrument 130. Based on the strength of the EM wave, the processor 160 is able to estimate a location of the instrument 130 with respect to the EM coordinate system. The EM sensor 185 may be installed on another element of the surgical system 100 to monitor the spatial relationship within the surgical system 100. The processor 160 may synchronize the EM coordinate system with the coordinate system of the 3D model.

As an alternative or in addition to incorporating the location of the tissue into the 3D model, a graphical representation of the tissue may be displayed at the corresponding location on a live video image of a surgical site, e.g., a video image obtained from an endoscope and displayed on a surgical display. The graphical representation may be overlaid or projected onto the live video image in an augmented way. Where video imaging is used, the location of the tissue may be synchronized with the video image, e.g., tissue features, surgical instrument(s), etc. within the video image, such that when the video image is moved or rotated, the graphical representation of the tissue is correspondingly moved or rotated.

Figure 2:
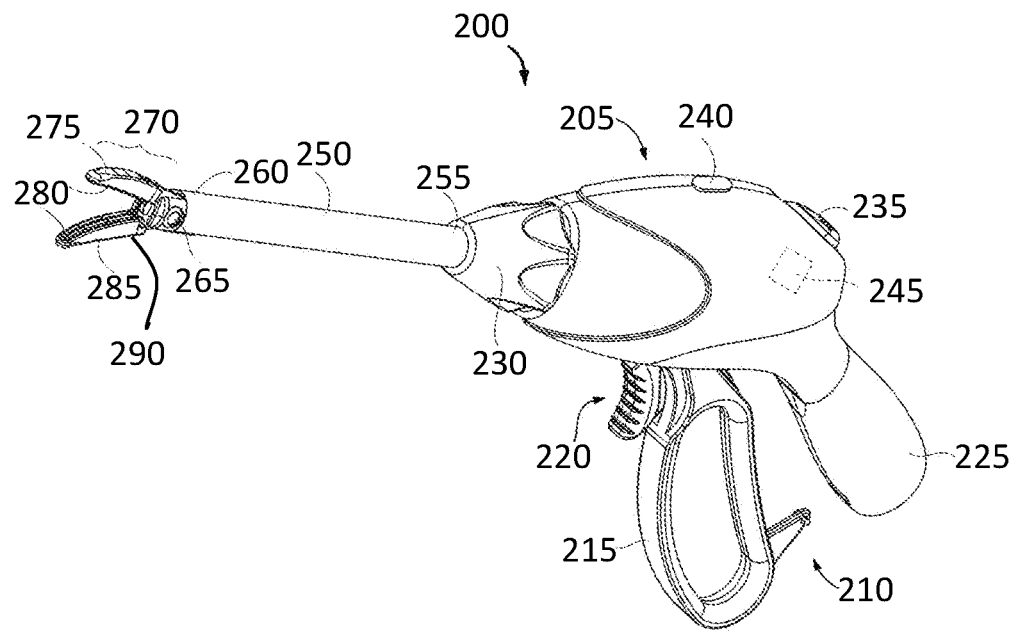
FIG. 2 is a perspective view of an energy-delivery device including an end effector assembly in accordance with aspects of the present disclosure.

FIG. 2 shows a forceps 200 for vessel sealing, as an example of the instrument 130 of FIG. 1, according to aspects of the present disclosure. The forceps 200 includes a housing 205, a handle assembly 210, a trigger assembly 220, a rotatable assembly 230, and an end effector assembly 270. The end effector assembly 270 may include any feature or combination of features of jaw members. The components of the forceps 200 are adapted to mutually cooperate to grasp, seal, divide and/or sense tissue, e.g., tubular vessels and vascular tissue. In aspects, the trigger assembly 220 may be configured to actuate a cutting function, e.g., a knife or electrical cutter, of the forceps 200 or to actuate another component, as described below.

The end effector assembly 270 generally includes two jaw members 275 and 285 disposed in opposing relation relative to one another. One or both of the jaw members 275 and 285 are movable from a first position wherein the jaw members 275 and 285 are disposed in spaced relation relative to one another to a second position wherein the jaw members 275 and 285 cooperate to grasp tissue therebetween.

The forceps 200 includes an elongated shaft 250 having a distal portion 260 configured to mechanically engage the end effector assembly 270. The proximal portion 255 of the shaft 250 is received within the housing 205. The rotatable assembly 230 is mechanically associated with the shaft 250 such that rotational movement of rotatable assembly 230 imparts similar rotational movement to the shaft 250 that, in turn, rotates the end effector assembly 270 relative to the housing 205.

The handle assembly 210 includes a fixed handle 225 and a movable handle 215. In aspects, the fixed handle 225 is integrally associated with the housing 205, and the movable handle 215 is selectively movable relative to the fixed handle 225. The movable handle 215 of the handle assembly 210 is ultimately connected to a drive assembly (not shown). As can be appreciated, applying force to move the movable handle 215 toward the fixed handle 225 pulls a drive sleeve of the drive assembly proximally to impart movement to the jaw members 275 and 285 from the first position, wherein the jaw members 275 and 285 are disposed in spaced relation relative to one another, to the second position, where the jaw members 275 and 285 cooperate to grasp tissue located therebetween.

At least one of the jaw members 275 and 285 may be equipped with a surface sensor 280. In aspects, the surface sensor 280 may be installed or affixed on the surface of each of the jaw members 275 and 285. The surface sensor 280 is capable of sensing a touch span reflecting the distance along the surface sensor 280 that touches tissue. When the surface sensor 280 senses the touching area or the touch span, which may be used to estimate the size of the tissue. The touch span or the touching area may be one position or an area.

In aspects, the surface sensor 280 may be an array of sensors incorporated into a contact surface of each jaw member 275, 285. Based on results from the array of sensors, proximal and distal sides of the tissue with respect to the end effector assembly 270 may be detected and used to detect the size of the tissue.

In aspects, the end effector assembly 270 may be configured as a unilateral assembly that includes a stationary jaw member mounted in fixed relation to the shaft 250 and a pivoting jaw member movably mounted about a pivot 265. Alternatively, the forceps 200 may include a bilateral assembly, e.g., both jaw members 275 and 285 move relative to one another and shaft 250. The jaw members 275 and 285 may be curved at various angles to facilitate manipulation of tissue and/or to provide enhanced line-of-sight for accessing targeted tissues.

In aspects, an angle sensor 290 may be incorporated into the end effector assembly 270. The angle sensor 290 may be installed on either or both of the jaw members 275 and 285 and configured to detect an angle between the two jaw members 275 and 285. The detected angle may also be used to estimate the size of the tissue.

In aspects, the angle sensor 290 may count a position of a jaw driver (e.g., a tube, shaft, etc.), such as 1, 2, 3, . . . , and n, where n may be the maximum count or a predetermined integer identifying a predetermined angle, such as 90 or 180 in degrees, or $\pi/2$ or $\pi$ in radians. The counted position is then used to convert the position of the jaw driver to an angle between the jaw members 275 and 285.

The forceps 200 further includes first and second switch assemblies 235 and 240 configured to selectively provide energy to the end effector assembly 270. More particularly, the first switch assembly 235 may be configured to perform a first type of surgical procedure (e.g., seal, cut, and/or sense) and a second switch assembly 240 may be configured to perform a second type of surgical procedure (e.g., seal, cut, and/or sense). It should be noted that the presently disclosed aspects may include any number of suitable switch assemblies and are not limited to the switch assemblies 235 and 240. It should further be noted that the presently disclosed aspects may be configured to perform any suitable surgical procedure and are not limited to only sealing, cutting and sensing. Further, as noted above, cutting may be performed by actuation of the trigger assembly 220, e.g., for mechanical cutting, in addition to or as an alternative to second switch assembly 240.

The forceps 200 may include a controller 245. In aspects, the controller 245 may be provided as a separate component coupled to the forceps 200 or integrated within the forceps 200. The controller 245 may include any type of computing device, computational circuit, or any type of processor or processing circuit capable of executing a series of instructions that are stored in a memory. The controller 245 may be configured to calculate, estimate, and control one or more operating parameters associated with an energy source (e.g., the power supply 110 or the energy output stage 120 (FIG. 1)) based on one or more signals indicative of user input, such as generated by the first and second switch assemblies 235 and 240 and/or one or more separate, user-actuatable buttons or switches. Examples of switch configurations that may be suitable for use with the forceps 200 include, but are not limited to, pushbutton, toggle, rocker, tactile, snap, rotary, slide and thumbwheel.

The controller 245 may estimate the size of the tissue grasped between the jaw members 275 and 285. When the surface sensor 280 senses a location of touch to the tissue, the controller 245 calculates a distance between the location and the pivot 265 and estimates the size of the tissue.

Figure 3A:
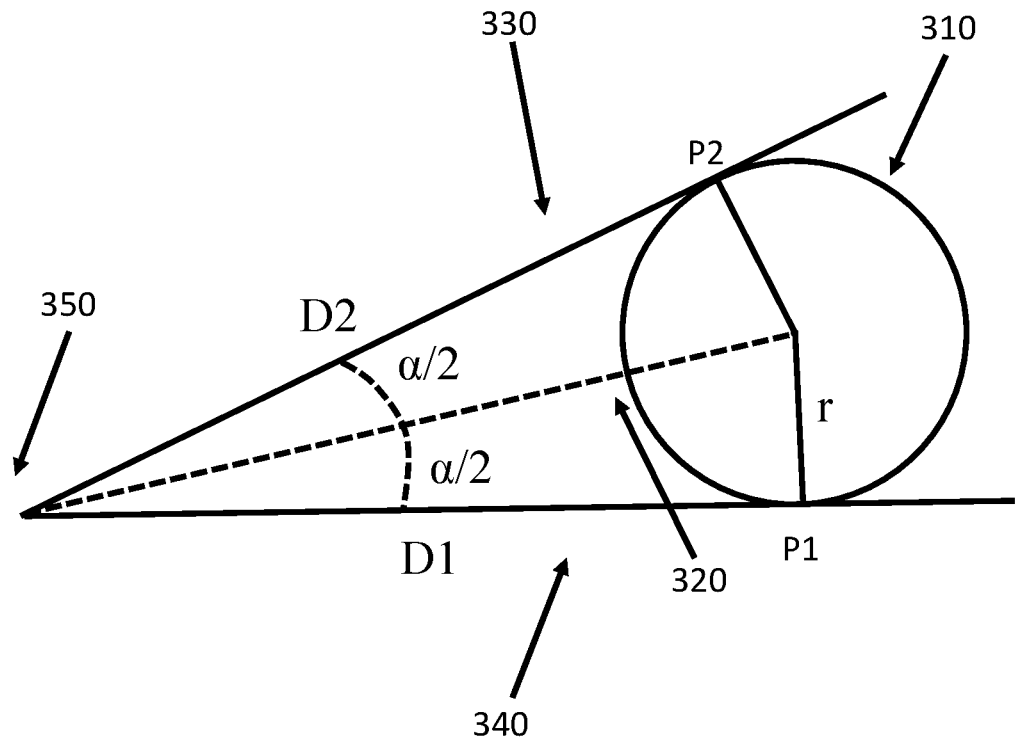
FIG. 3A is a simplified graphical illustration for estimating the size of the tissue according to aspects of the present disclosure.

FIG. 3A illustrates an aspect for estimating a radius or diameter of the tissue as the size of the tissue according to this disclosure. With reference to FIGS. 2 and 3A, the upper line 330 and the lower line 340 represent the opposing surfaces of the two jaw members 275 and 285 of the forceps 200, respectively, or the surface sensor 280 of the two jaw members 275 and 285, and a circle 310 represents tissue, e.g., a vessel. When the two jaw members 275 and 285 grasp the tissue 310, the surface sensor installed on the surfaces of the two jaw members 275 and 285 touches the tissue 310 at a first touch location P1 and a second touch location P2. The first distance between a pivot 350 and the first touch location P1 is represented as D1 and the second distance between the pivot 350 and the second touch location P2 is represented as D2. When the jaw members 275 and 285 touch the tissue 310 at an area, the first or second touch location may be a center position of the contacted area.

In some aspects, the cross-section of the tissue 310 is assumed to be a full circle and thus the first distance D1 is equal to the second distance D2. The angle sensor may detect an angle $\alpha$ between the two jaw members 275 and 285. When a center line 320 is connected between the pivot 350 and the center of the tissue 310, the center line dissects the angle $\alpha$ so that the angle between the center line 320 and the lower line 340 becomes $\alpha/2$.

The radius of the tissue 310 is then calculated by the following equation:

$$r = D1 * \tan\left(\frac{\alpha}{2}\right).$$

The radius r may be used as the size of the tissue. In aspects, the size of the tissue 310 may be the diameter of the tissue, that is 2*r.

In other aspects, the tissue 310 is not assumed to have a full circle cross-section but may have an elliptic, convex, or other shape. In this case, the first distance D1 may not be equal to the second distance D2. The size of the tissue 310 may be estimated based on the first and second distances D1 and D2 and the angle $\alpha$. The size of the tissue 310 may be estimated by one of the following equations:

$$S = (D1 + D2) * \tan\left(\frac{\alpha}{2}\right);$$

$$S = 2 * MAX(D1, D2) * \tan\left(\frac{\alpha}{2}\right); \text{ and}$$

$$S = 2 * MIN(D1, D2) * \tan\left(\frac{\alpha}{2}\right),$$

where S is the size of the tissue 310, MAX is a function outputting the maximum, and MIN is a function outputting the minimum. The equations, however, are not limited to the list above but can be any equation that a person of ordinary skill in the art reading this disclosure would readily appreciate.

In some instances, the two jaw members may not touch the tissue 310 at the same time. Under this situation, the angle α may be measured at a time when both of the two jaw members touch the tissue.

In various aspects, the size of the tissue 310 may be estimated several times, e.g., at various times during grasping, prior to delivery of energy for performing surgical operations. For example, when the two jaw members further grasp the tissue 310, the surface sensor may detect additional touch points. The distance between a proximal touch location and a distal touch location may be used to estimate the size with an angle difference between the initial angle α and the current angle, where the proximal touch point and the distal touch point are the two end touch points. The controller 245 may perform basic mathematical operations or use empirical data to estimate the size of the grasped tissue 310.

In various aspects, the controller 245 may employ machine learning algorithm to provide an estimate for the size of the tissue from the several estimates prior to the delivery of energy or surgical operations.

Figure 3B:
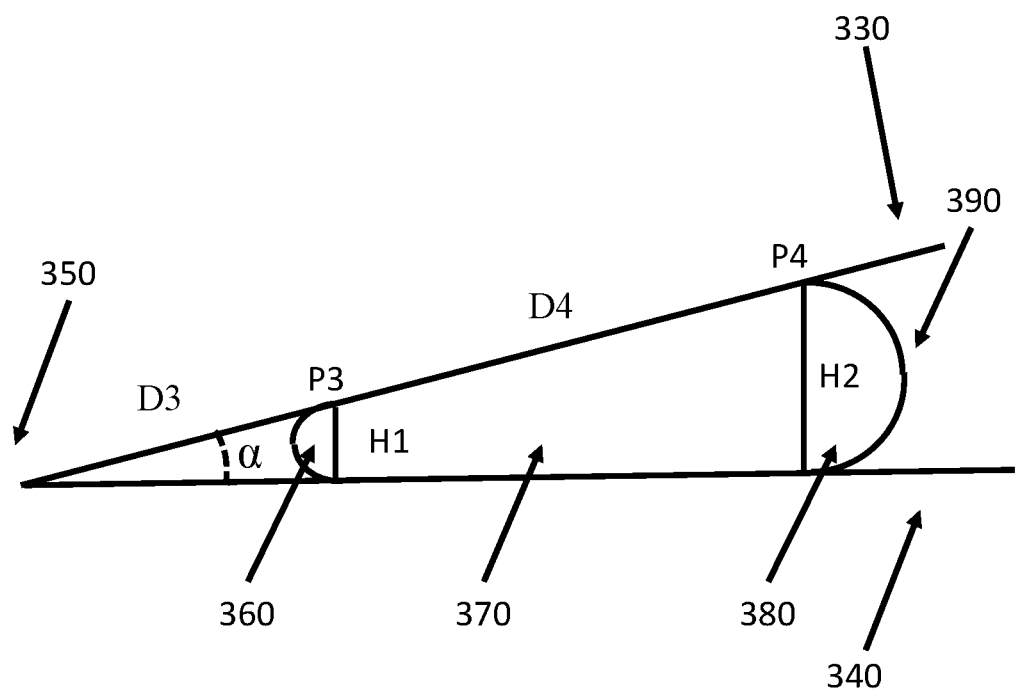
FIG. 3B is another simplified graphical illustration for estimating the size of the tissue according to aspects of the present disclosure.

FIG. 3B illustrates an illustrative method for estimating a mass of the tissue as the size of the tissue according to this disclosure. When two jaw members 275 and 285 grasp the tissue 310, the surface sensors installed on the surfaces of the two jaw members 275 and 285 press the tissue 390 along the length direction of the jaw members 275, 285 from the proximal touch location P3 to the distal touch location P4. D3 represents a distance between the pivot 350 and the proximal touch location P3 and the length D4 of the touch span is a distance between the proximal and distal touch locations P3 and P4.

The angle sensor may detect an angle α between the two jaw members 275 and 285. Based on the lengths D3, D4, and the angle α, the heights H1 and H2 from the lower jaw member 285 to the touch locations P3 and P4 are calculated, respectively, as follows:

$$H1 = D3 * \sin(\alpha); \text{ and}$$

$$H2 = D4 * \sin(\alpha).$$

In aspects, the proximal and distal portions of the grasped tissue may be bulged due to the pressure exerted thereon by the two jaw members 275 and 285. The bulged portions may be close to a half circle on each end. Under this assumption, the grasped tissue 390 may be divided into three portions. The first portion 360 is the half circle which is the bulged portion at the proximal end of the grasped tissue 390, the second portion 360 is the trapezoidal portion in the middle of the grasped tissue 390, and the third portion 380 is another half circle at the distal end of the grasped tissue 390. Thus, the cross-sectional area of the grasped tissue 390 may be estimated by adding areas of the first, second, and third portions 360-380.

Each area of the three portions may be calculated by the following equations:

$$S1 = \frac{\pi * \left(\frac{H1}{2}\right)^2}{2};$$

$$S2 = \frac{(H1 + H2)}{2} * D4 * \cos(\alpha); \text{ and}$$

$$S3 = \frac{\pi * \left(\frac{H2}{2}\right)^2}{2},$$

where S1 is the cross-sectional area of the first portion 360, S2 is the cross-sectional area of the second portion 370, and S3 is the cross-sectional area of the third portion 380. Thus, the total cross-sectional area of the grasped tissue is S1+S2+S3. Then, the volume of the grasped tissue may be calculated by multiplying the cross-sectional area by the width of the first or second jaw member 275, 285, and the mass of the grasped tissue may be calculated by multiplying the volume to the density of the grasped tissue 390.

Referring back to FIG. 2, the first and second switch assemblies 235 and 240 may also cooperate with the controller 245, which may be configured to trigger one of the switches to automatically change between a first mode (e.g., sealing mode) and a second mode (e.g., cutting mode) upon the detection of one or more parameters or thresholds. In aspects, the controller 245 is configured to receive feedback information, including various sensor feedback with regard to temperature of tissue, electrical impedance of tissue, jaw closure pressure, jaw positioning, and/or other various feedback information, e.g., using Raman spectroscopy, laser speckle imaging, optical imaging, fluorescence spectroscopy, and/or laser-induced tissue fluorescence, and to control the energy source based on the feedback information.

Aspects of the present disclosure allow the jaw members 275 and 285 to seal and/or cut tissue using light energy, ultrasonic energy, and/or RF energy. The controller 245 may include a feedback loop that indicates the size of the tissue so that an appropriate amount of energy is supplied to treat the tissue. An audible or visual feedback monitor may be employed to convey information of the size. For example, the feedback may be a LED (light emitting diode) light. When the tissue is large, meaning that the size is greater than or equal to 5 millimeters, the feedback may be a red light, e.g., informing the clinician to reconsider treating tissue that large, preventing energy activation on tissue that large, adjusting the mechanical and/or energy parameters, etc. If the tissue is an average size, meaning that the size is greater than or equal to 2 millimeters and less than 5 millimeters, a green light is lit. When the size of the tissue is small, meaning that the tissue is less than 2 millimeters, a yellow light is lit, e.g., providing a warning, informing the clinician to adjust the mechanical and/or energy parameters, etc. It is also contemplated that other vessel diameters, whose diameter is up to 7 millimeters, be associated with the light indicator and may be sealed. The mode for delivering the feedback related to the size of the tissue is not limited to the visual and optical means but can be extended to include textual information or different audio sounds corresponding to sizes of different tissue.

In aspects, the surgical system 100 may be a robotic surgical system, which includes one or more robotic arms. The forceps 200 may be incorporated into or fixedly installed at one robotic arm with modifications as understood by one of ordinary skilled in the art to adapt a handheld device to one for use with a robotic surgical system.

Figure 4A:
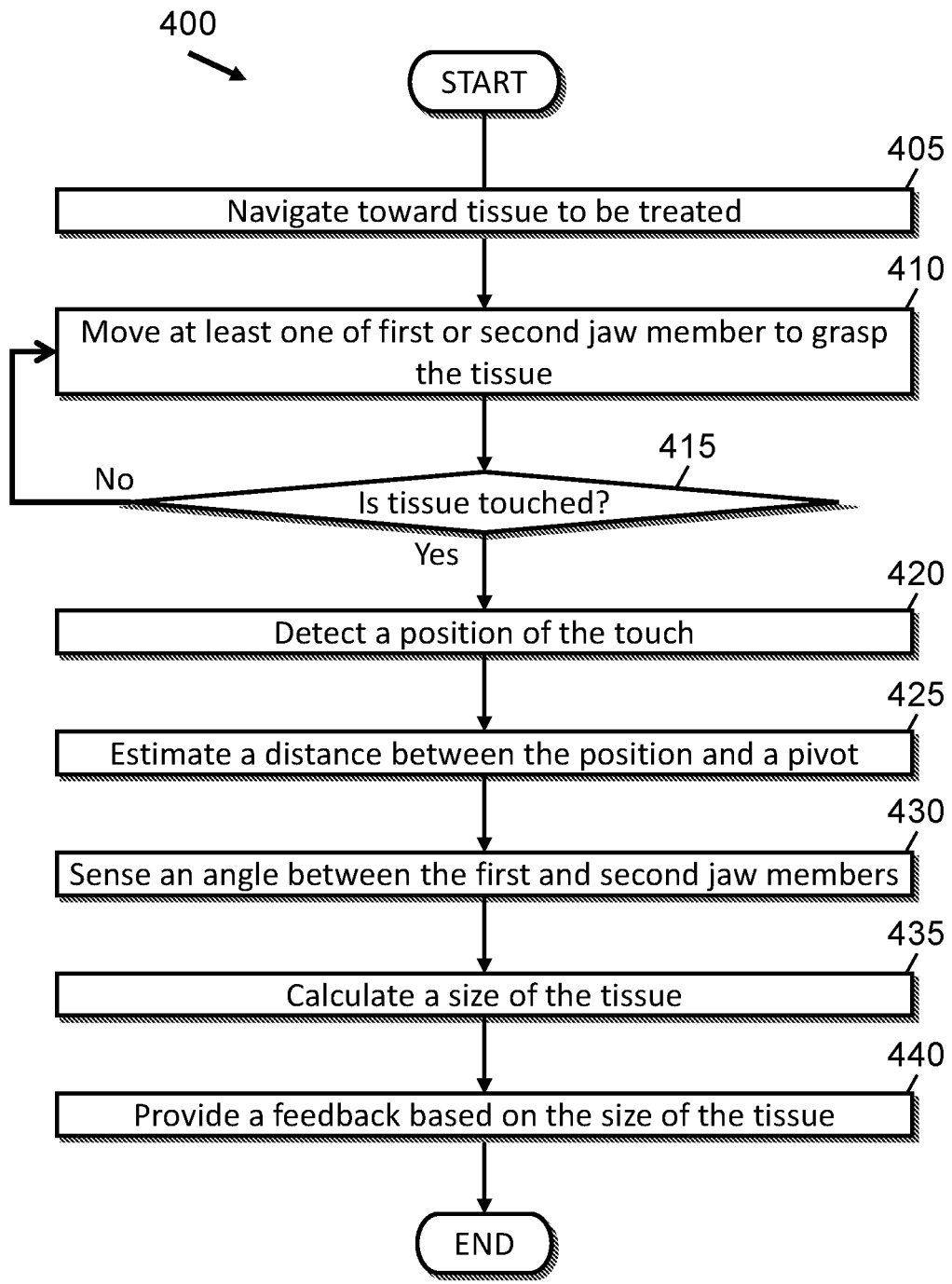
FIG. 4A is a flowchart illustrating a method for estimating a size of the tissue according to aspects of the present disclosure.

FIG. 4A shows a flowchart illustrating a method 400 for estimating a radius as a size of tissue grasped by two jaw members of an end effector in accordance with aspects of this disclosure. The method 400 starts by navigating a surgical instrument toward target tissue to be treated in step 405. The end effector of the surgical instrument may include first and second jaw members for grasping and treating the target tissue. A 3D model may provide a navigation path to the target tissue or a live view video may provide a clinician a live guide to the target tissue. In aspects, additional aids (e.g., global positioning system (GPS) based on EM waves, fluorescent implant, etc.) may also provide the clinician further clarity that the surgical instrument is navigating to the target tissue or following the navigation path.

When the surgical instrument arrives at the target tissue, at least one of the first or second jaw member may move to the other jaw member to grasp the tissue in step 410. The first and jaw members may include a surface sensor installed on the surface of the first and second jaw members. Thus, when the tissue touches the surface of one of the first and second jaw members, the surface sensor may detect a touch point where the tissue touches.

In step 415, it is determined whether or not the tissue touches the surface sensor of the two jaw members. The surface sensor may be a pressure sensor or a touch sensor. The surface sensor may detect a touch point where the tissue touches the surface sensor. When it is determined that the tissue does not touch the surface sensor, step 410 is repeatedly performed until the tissue touches the surface sensor.

When it is determined that the tissue touches the surface sensor, the surface sensor detects a touch point in step 420. A controller of the surgical instrument may estimate a distance between the touch point and a pivot where the two jaw members rotatably move in step 425.

In step 430, an angle sensor may sense an angle between the first and second jaw members about the pivot. Based on the distance and the angle, a size of the tissue may be estimated in step 435. For example, the size of the tissue may be estimated by the following equation:

$$S = 2*D*\tan\left(\frac{\alpha}{2}\right),$$

where S is the size of the tissue, D is the distance, and α is the angle.

Based on the size of the tissue, a feedback may be provided to a clinician or the surgical instrument. The feedback may be an LED light. The LED emits red when the size is large. When red is lit, for example, the clinician may be informed that a higher and/or longer energy is needed as compared to average-size tissue. Alternatively, as another example, the red light may be a warning to the clinical to re-grasp a smaller bite of tissue. A green light may be lit when the tissue is average size, and yellow light may be lit when the tissue is smaller than the average size. Based on the color of light, the clinician may manually control or adjust the energy-delivery parameters, may determine whether to proceed or re-grasp tissue, or may otherwise determine an appropriate course of action based on the indicated size of tissue.

In aspects, the feedback is an analog/digital signal to the controller 160 (FIG. 1) of the surgical instrument. Upon reception of the feedback signal, the controller may automatically adjust the energy-delivery parameters. That is, in aspects, a first energy-delivery algorithm may be utilized for large tissue, a second, different energy-delivery algorithm may be used for average tissue, and a third, still a different energy-delivery algorithm may be used for small tissue. Other configurations are also contemplated. The different algorithms may provide different amounts of energy, different periods of delivery of the energy, etc. The feedback signal is not limited to the light or analog/digital signal but can be any means that a person of skill in the art would readily perceive.

Figure 4B:
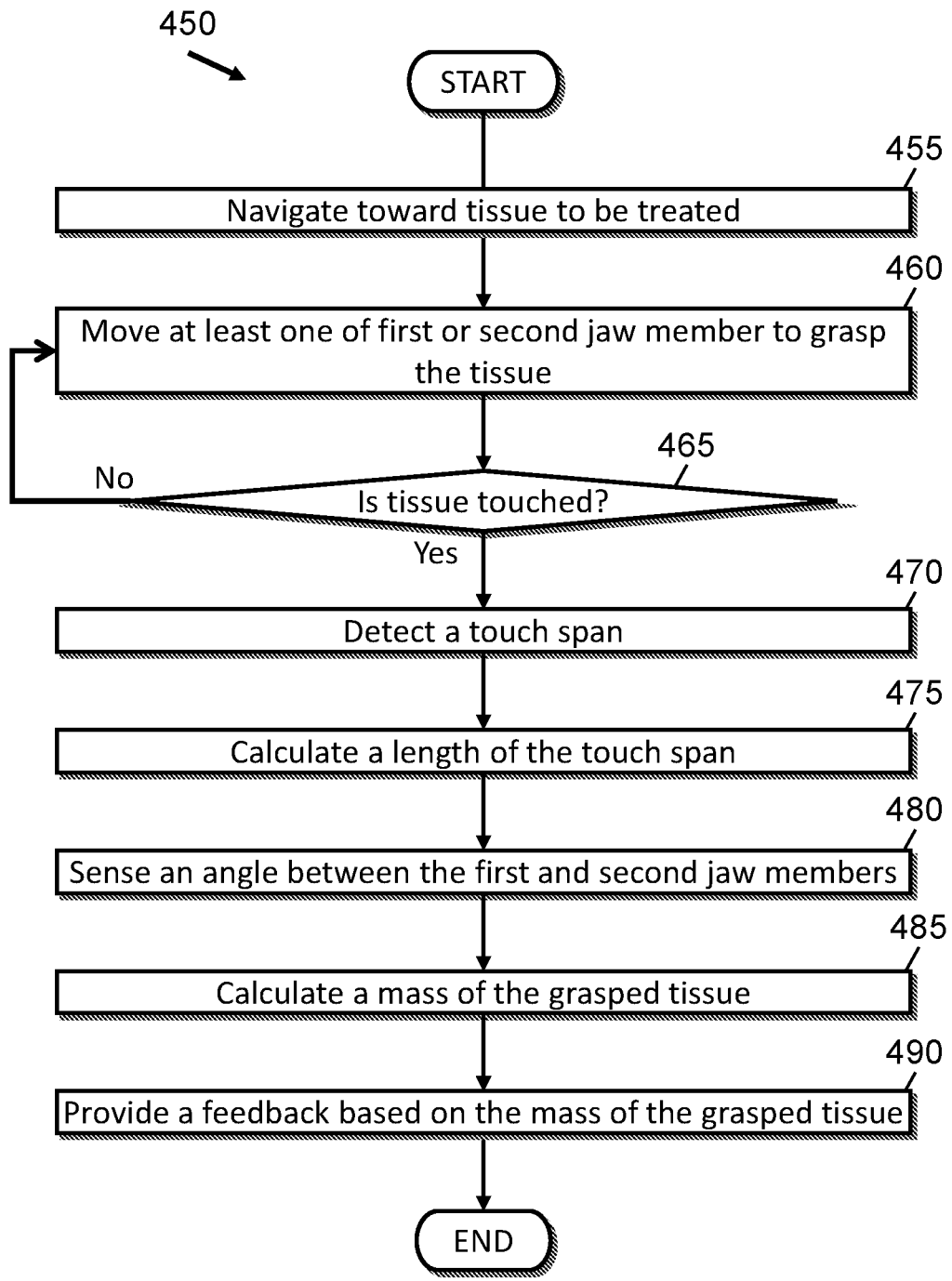
FIG. 4B is another flowchart illustrating a method for estimating a size of the tissue according to aspects of the present disclosure.

FIG. 4B shows another flowchart illustrating a method 450 for estimating a mass as a size of tissue grasped by two jaw members of an end effector in accordance with aspects of the disclosure. The method 450 performs the same steps 405-415 of the method 400 of FIG. 4A by navigating a surgical instrument toward target tissue to be treated in step 455, moving at least one of the first and second jaw members to grasp the tissue in step 460, and determining whether the tissue is touched in step 465.

When it is determined that the tissue touches the surface sensor, the surface sensor detects a touch span, which is distance along at least one of the jaw members where the tissue touches, in step 470. The proximal terminus of the touch span is a position closest to the pivot, and the distal terminus of the touch span is a position farthest from the pivot. Based on the proximal and distal termini of the touch span, the size of the touch span or a length of the touch span may be calculated in step 475.

In step 480, an angle sensor may sense an angle between the first and second jaw members with respect to the pivot when the first and second jaw members grasp the tissue. Based on the angle and the distance between the proximal and distal termini of the touch span, a size of the tissue may be estimated in step 485. In particular, a cross-sectional area may be used as the size of the tissue. The cross-sectional area of the grasped tissue may be estimated by adding the areas of the three portions of the grasped tissue as described above with respect to FIG. 3B.

In aspects, the cross-sectional area may be multiplied by a width of one of the first and second jaw members so as to obtain a volume of the grasped tissue. Then, the volume may be multiplied by the density (actual or estimated) of the grasped tissue and the width of the first or second jaw member so as to obtain a mass of the grasped tissue. The mass may be used as the size of the tissue to determine an appropriate course of action to treat the tissue.

Based on the size of the tissue, a feedback may be provided to a clinician or the surgical instrument in step 490. The feedback may be an LED light. The LED emits, for example, red when the size is large. When red is lit, for example, the clinician may be informed that a higher and/or longer energy is needed as compared to average-size tissue. Alternatively, as another example, the red light may be a warning to the clinical to re-grasp a smaller bite of tissue. A green light may be lit when the tissue is average size, and yellow light may be lit when the tissue is smaller than the average size. Based on the color of light, the clinician may manually control or adjust the energy-delivery parameters, may determine whether to proceed or re-grasp tissue, or may otherwise determine an appropriate course of action based on the indicated size of tissue.

In aspects, the feedback is an analog/digital signal to the controller 160 (FIG. 1) of the surgical instrument. Upon reception of the feedback signal, the controller may automatically adjust the energy-delivery parameters. That is, in aspects, a first energy-delivery algorithm may be utilized for large tissue, a second, different energy-delivery algorithm may be used for average tissue, and a third, still a different energy-delivery algorithm may be used for small tissue. Other configurations are also contemplated. The different algorithms may provide different amounts of energy, different periods of delivery of the energy, etc. The feedback signal is not limited to the light or analog/digital signal but can be any means that a person of skill in the art would readily perceive.

Figure 5:
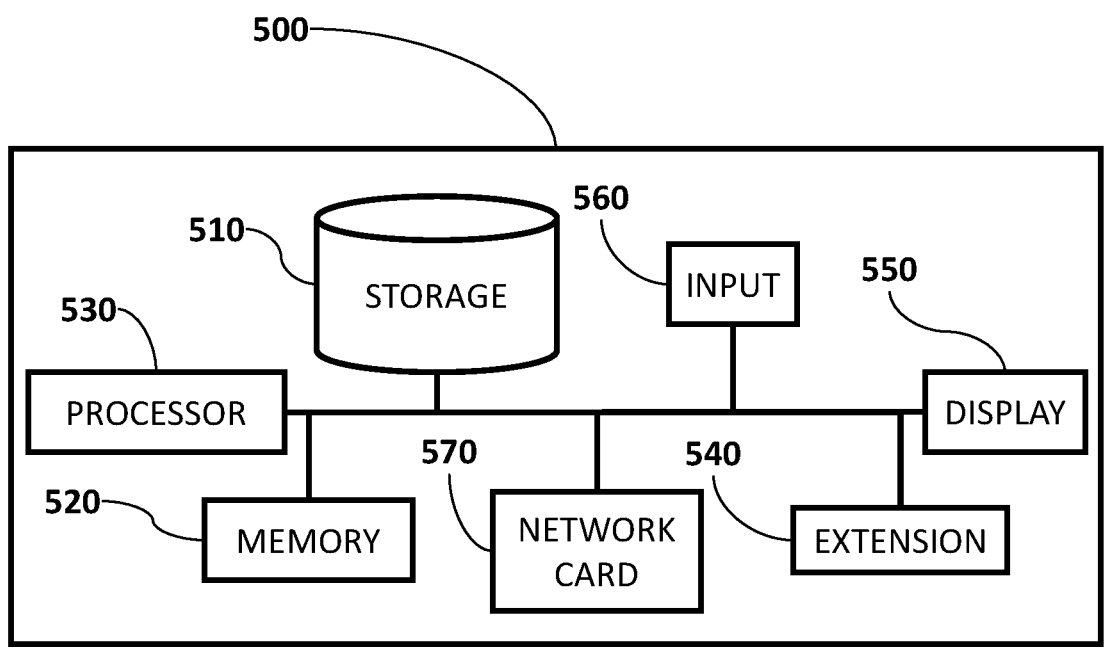
FIG. 5 is a block diagram for a computing device according to aspects of the present disclosure.

FIG. 5 is a block diagram for a computing device 500 representative of combination of the processor 160, the display 170, the user interface 165, and the memory 175 of FIG. 1 or the controller 245 of FIG. 2 in accordance with aspects of the present disclosure. The computing device 500 may include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, embedded computers, and autonomous vehicles. Those of skill in the art will recognize that many smartphones are suitable for use in the system described herein. Suitable tablet computers include those with booklet, slate, and convertible configurations, known to those of skill in the art.

In aspects, the computing device 500 includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In aspects, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In aspects, the computing device 500 may include a storage 510. The storage 510 is one or more physical apparatus used to store data or programs on a temporary or permanent basis. In aspects, the storage 510 may be volatile memory and requires power to maintain stored information. In aspects, the storage 510 may be non-volatile memory and retains stored information when the computing device 500 is not powered. In aspects, the non-volatile memory includes flash memory. In aspects, the non-volatile memory includes dynamic random-access memory (DRAM). In aspects, the non-volatile memory includes ferroelectric random-access memory (FRAM). In aspects, the non-volatile memory includes phase-change random access memory (PRAM). In aspects, the storage 510 includes, by way of non-limiting examples, CD-ROMs, DVDs, flash memory devices, magnetic disk drives, magnetic tapes drives, optical disk drives, and cloud computing-based storage. In aspects, the storage 510 may be a combination of devices such as those disclosed herein.

The computing device 500 further includes a processor 530, an extension 540, a display 550, an input device 560, and a network card 570. The processor 530 is a brain to the computing device 500. The processor 530 executes instructions which implement tasks or functions of programs. When a user executes a program, the processor 530 reads the program stored in the storage 510, loads the program on the RAM, and executes instructions prescribed by the program.

The processor 530 may include a microprocessor, central processing unit (CPU), application specific integrated circuit (ASIC), arithmetic coprocessor, graphic processor, or image processor, each of which is electronic circuitry within a computer that carries out instructions of a computer program by performing the basic arithmetic, logical, control and input/output (I/O) operations specified by the instructions.

In aspects, the extension 540 may include several ports, such as one or more universal serial buses (USBs), IEEE 1394 ports, parallel ports, and/or expansion slots such as peripheral component interconnect (PCI) and PCI express (PCIe). The extension 540 is not limited to the list but may include other slots or ports that can be used for appropriate purposes. The extension 540 may be used to install hardware or add additional functionalities to a computer that may facilitate the purposes of the computer. For example, a USB port can be used for adding additional storage to the computer and/or an IEEE 1394 may be used for receiving moving/still image data.

In aspects, the display 550 may be a cathode ray tube (CRT), a liquid crystal display (LCD), or light emitting diode (LED). In aspects, the display 550 may be a thin film transistor liquid crystal display (TFT-LCD). In aspects, the display 550 may be an organic light emitting diode (OLED) display. In various aspects, the OLED display is a passive-matrix OLED (PMOLED) or active-matrix OLED (AMOLED) display. In aspects, the display 550 may be a plasma display. In aspects, the display 550 may be a video projector. In aspects, the display may be interactive (e.g., having a touch screen or a sensor such as a camera, a 3D sensor, etc.) that can detect user interactions/gestures/responses and the like.

In still other aspects, the display 550 is a combination of devices such as those disclosed herein.

A user may input and/or modify data via the input device 560 that may include a keyboard, a mouse, or any other device with which the use may input data. The display 550 displays data on a screen of the display 550. The display 550 may be a touch screen so that the display 550 can be used as an input device.

The network card 570 is used to communicate with other computing devices, wirelessly or via a wired connection. Through the network card 570, the computing device 500 may receive, modify, and/or update data from and to a managing server.

The aspects disclosed herein are examples of the disclosure and may be embodied in various forms. For instance, although certain aspects herein are described as separate aspects, each of the aspects herein may be combined with one or more of the other aspects herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, C#, Delphi, Fortran, Java, JavaScript, machine code, operating system command languages, Pascal, Perl, PL1, scripting languages, Visual Basic, meta-languages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An electrosurgical instrument comprising:
    an end effector assembly including first and second jaw members, at least one of the first or second jaw members movable about a pivot relative to the other from a spaced-apart position to an approximated position to grasp tissue between first and second opposed surfaces of the first and second jaw members, respectively; and
    an interface configured to provide a feedback related to at least one of a size or a mass of the tissue grasped by the first and second jaw members,
    wherein at least one of the first or second jaw members includes at least one touch sensor configured to sense a proximal touch span where a proximal portion of the tissue touches at least one of the first or second opposed surfaces and to sense a distal touch span where a distal portion of the tissue touches at least one of the first or second opposed surfaces,
    wherein the end effector assembly further includes an angle sensor configured to sense an angle α about the pivot between the first and second opposed surfaces, and
    wherein a controller associated with the interface is configured to:
        determine a first distance between the pivot and the proximal touch span;
        determine a second distance between the pivot and the distal touch span; and
        estimate the at least one of size or the mass of the tissue based upon the first and second distances and the angle α, wherein estimating the at least one of the size or mass of the grasped tissue takes into account at least one portion of tissue that is spaced from the first and second opposed surfaces and outside a region defined between the proximal and distal touch spans.

2. The electrosurgical instrument according to claim 1, wherein the proximal and distal touch spans are first and second positions, and the at least one touch sensor provides the first and second distances as distances D1 and D2 between the pivot and the first and second positions, respectively.

3. The electrosurgical instrument according to claim 1, wherein the touch sensor is a pressure sensor or a contact sensor.

4. The electrosurgical instrument according to claim 1, wherein a cross-sectional area of the grasped tissue is calculated based at least in part on the first and second distances and the angle α.

5. The electrosurgical instrument according to claim 4, wherein the mass of the grasped tissue is calculated by multiplying the cross-sectional area, a width of the first or second jaw member, and a density of the grasped tissue.

6. The electrosurgical instrument according to claim 1, wherein the feedback indicates that the grasped tissue is ready to be sealed when the at least one of the size or the mass of the grasped tissue is less than a first threshold.

7. The electrosurgical instrument according to claim 6, wherein the feedback is a green light.

8. The electrosurgical instrument according to claim 6, wherein, when the at least one of the size or the mass of the grasped tissue is greater than or equal to the first threshold and less than a second threshold, the feedback indicates that the grasped tissue is ready to be sealed with different energy-delivery parameters than when the at least one of the size or the mass is less than the first threshold.

9. The electrosurgical instrument according to claim 8, wherein the feedback is a yellow light.

10. The electrosurgical instrument according to claim 8, wherein the feedback indicates that the grasped tissue cannot be sealed when the at least one of the size or the mass is greater than or equal to the second threshold.

11. The electrosurgical instrument according to claim 10, wherein the feedback is a red light.

12. A method for controlling an electrosurgical instrument including an end effector assembly having first and second jaw members, at least one of the first or second jaw members movable about a pivot relative to the other from a spaced-apart position to an approximated position to grasp tissue between first and second opposed surfaces of the first and second jaw members, respectively, the method comprising:
    moving at least one of the first or second jaw members about the pivot to grasp tissue;
    sensing a proximal touch span on at least one of the first or second opposed surfaces;
    determining a first distance between the pivot and the tissue based on the proximal touch span;
    sensing a distal touch span on at least one of the first or second opposed surfaces;
    determining a second distance between the pivot and the tissue based on the distal touch span;
    sensing an angle α between the first and second opposed surfaces about the pivot;
    estimating at least one of a size or a mass of the grasped tissue based on the first and second distances and the angle α, wherein estimating the at least one of the size or the mass of the grasped tissue takes into account at least one portion of tissue that is spaced from the first and second opposed surfaces and outside a region defined between the proximal and distal touch spans; and
    providing a feedback based on the at least one of the size or the mass of the tissue.

13. The method according to claim 12, wherein the proximal and distal touch spans are first and second positions, and the method further comprises determining first and second distances D1 and D2 between the pivot and the first and second positions, respectively.

14. The method according to claim 12, wherein estimating the at least one of the size or the mass of the tissue includes calculating a cross-sectional area of the grasped tissue based at least in part on the first and second distances and the angle α.

15. The method according to claim 14, wherein estimating the mass of the grasped tissue by multiplying the cross-sectional area, a width of the first or second jaw members, and a density of the grasped tissue.

16. The method according to claim 12, wherein the feedback indicates that the grasped tissue is ready to be sealed when the at least one of the size or the mass of the grasped tissue is less than a first threshold.

17. The method according to claim 16, wherein the feedback is a green light.

18. The method according to claim 16, wherein, when the at least one of the size or the mass is greater than or equal to the first threshold and less than a second threshold, the feedback indicates that the grasped tissue is ready to be sealed with different energy-delivery parameters than when the at least one of the size or the mass is less than the first threshold.

19. The method according to claim 18, wherein the feedback is a yellow light.

20. The method according to claim 18, wherein the feedback indicates that the grasped tissue cannot be sealed when the size is greater than or equal to the second threshold.

21. The method according to claim 20, wherein the feedback is a red light.

22. A nontransitory storage medium storing instructions that, when executed by a processor, cause the processor to perform a method for controlling an electrosurgical instrument including an end effector assembly having first and second jaw members, at least one of the first or second jaw members movable about a pivot relative to the other from a spaced-apart position to an approximated position to grasp tissue between first and second opposed surfaces of the first and second jaw members, respectively, the method comprising:
    moving at least one of the first or second jaw members about the pivot to grasp tissue;
    sensing a proximal touch span on at least one of the first or second opposed surfaces;
    determining a first distance between the pivot and the tissue based on the proximal touch span;
    sensing a distal touch span on at least one of the first or second opposed surfaces;
    determining a second distance between the pivot and the tissue based on the distal touch span;
    sensing an angle α between the first and second opposed surfaces about the pivot;
    estimating at least one of a size or a mass of the tissue based on the first and second distances and the angle α, wherein estimating the at least one of the size or the mass of the tissue takes into account at least one portion of tissue that is spaced from the first and second opposed surfaces and outside a region defined between the proximal and distal touch spans; and
    providing a feedback based on the at least one of size or the mass of the tissue.

\* \* \* \* \*